United States Patent [19]

Squire

[11] 4,302,608

[45] Nov. 24, 1981

[54] PROCESS FOR THE ISOMERIZATION OF HEXAFLUOROPROPYLENE OXIDE TO HEXAFLUOROACETONE

[75] Inventor: Edward N. Squire, Glen Mills, Pa.

[73] Assignee: E. I. Du Pont de Nemours and Company, Wilmington, Del.

[21] Appl. No.: 179,812

[22] Filed: Aug. 20, 1980

[51] Int. Cl.$^3$ ............................................. C07C 45/58
[52] U.S. Cl. ..................................................... 568/384
[58] Field of Search .............................. 568/384, 386; 260/544 F

[56] References Cited

U.S. PATENT DOCUMENTS

| | | | |
|---|---|---|---|
| 3,213,134 | 10/1965 | Morin | 260/544 F |
| 3,321,515 | 5/1967 | Moore et al. | 568/384 |
| 3,358,003 | 12/1967 | Eleuterio et al. | 260/544 F |
| 3,542,883 | 11/1970 | Nenitesch et al. | 568/384 |
| 3,855,303 | 12/1974 | Bishop | 568/384 |
| 3,925,495 | 12/1975 | Rodewald | 585/372 |
| 4,238,416 | 12/1980 | Tohzuka et al. | 568/384 |

OTHER PUBLICATIONS

Zapevalor et al., Zh. Org. Khim., vol. 1975, 11(8) 1608-1611 (1975).
Zapevalor et al., Chem. Abst., vol. 80, #26713m (1974).
Zanaenos et al., Izn. Akad Nauk SSSR, Ser. Khim, 1974 (10), p. 2391, 1974.

*Primary Examiner*—Natalie Trousof
*Assistant Examiner*—James H. Reamer

[57] ABSTRACT

A continuous process for the isomerization of hexafluoropropylene oxide to hexafluoroacetone comprises passing hexafluoropropylene oxide in contact with liquid antimony pentafluoride adsorbed on a solid support under conditions which substantially prevent loss of antimony pentafluoride from the reactor in which the isomerization is carried out and removing the hexafluoroacetone product at about the same rate as that at which it is formed. Hexafluoroacetone is an important industrial monomer, which can be copolymerized, for example, with ethylene and tetrafluoroethylene to a product that finds use in coating electrical wires.

10 Claims, 2 Drawing Figures

PROCESS FOR THE ISOMERIZATION OF HEXAFLUOROPROPYLENE OXIDE TO HEXAFLUOROACETONE

BACKGROUND OF THE INVENTION

Hexafluoroacetone is becoming an important chemical, which finds use as an intermediate to other fluorocarbon chemicals as well as a monomer in the manufacture of certain fluoropolymers.

The normal commercial process for making hexafluoroacetone requires two steps: (1) chlorination of acetone to hexachloroacetone, and (2) conversion of hexachloroacetone to hexafluoroacetone. Although high-purity product can be obtained in good yields by this process, a cheaper route, requiring only one step, would be highly desirable. Hexafluoropropylene oxide, an industrial perfluorocarbon intermediate, can be isomerized to hexafluoroacetone in the presence of antimony pentafluoride solution as shown in U.S. Pat. No. 3,213,134 to Morin. Although this patent demonstrates the principle, it certainly does not disclose a practical process. The isomerization of hexafluoropropylene oxide was carried out during a period of 20 hours in a sealed glass ampoule at 90° C. A practical process should ideally be capable of continuous, rather than batch, operation; so that isomerization will be virtually instantaneous or at least very fast, rather than time-consuming.

SUMMARY OF THE INVENTION

According to this invention, there is now provided a continuous process for the isomerization of hexafluoropropylene oxide to hexafluoroacetone, said process comprising contacting in a reactor, at a temperature of about 10°–200° C., a stream of gaseous hexafluoropropylene oxide at an absolute pressure of about 0.103–13.79 MPa with a catalyst consisting essentially of liquid antimony pentafluoride adsorbed on a solid support; hexafluoroacetone being removed from the reactor at essentially the same rate as that at which it is formed; and a portion of the reactor close to the hexafluoroacetone removal point being cooled to prevent loss of antimony pentafluoride.

DETAILED DESCRIPTION OF THE INVENTION

Hexafluoropropylene oxide, sometimes abbreviated as HFPO, which is the starting material in the instant process, can be made by the epoxidation of hexafluoropropylene, for example, as taught in U.S. Pat. No. 3,358,003 to Eleuterio et al. Since hexafluoropropylene oxide is a gas at atmospheric pressure (boiling point about −28° C.), it will be usually available in cylinders from which it either can be dispensed at the desired pressure or pumped to the desired pressure.

Antimony pentafluoride is a liquid at atmospheric pressure (b.p. 150° C.). It is commercially available from Allied Chemical Co. This chemical is toxic, very hygroscopic and reactive and, therefore, must be handled carefully and in the absence of moisture.

The product, hexafluoroacetone, sometimes abbreviated as HFA, is a gas at atmospheric pressure (boiling point about −27° C.) This material is considered toxic and may be teratogenic. Accordingly, it must be handled with great caution.

The isomerization reaction is illustrated by the following equation:

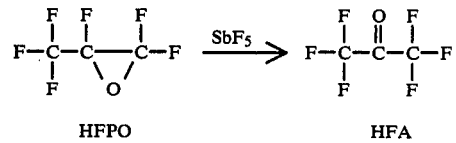

Figure 1:
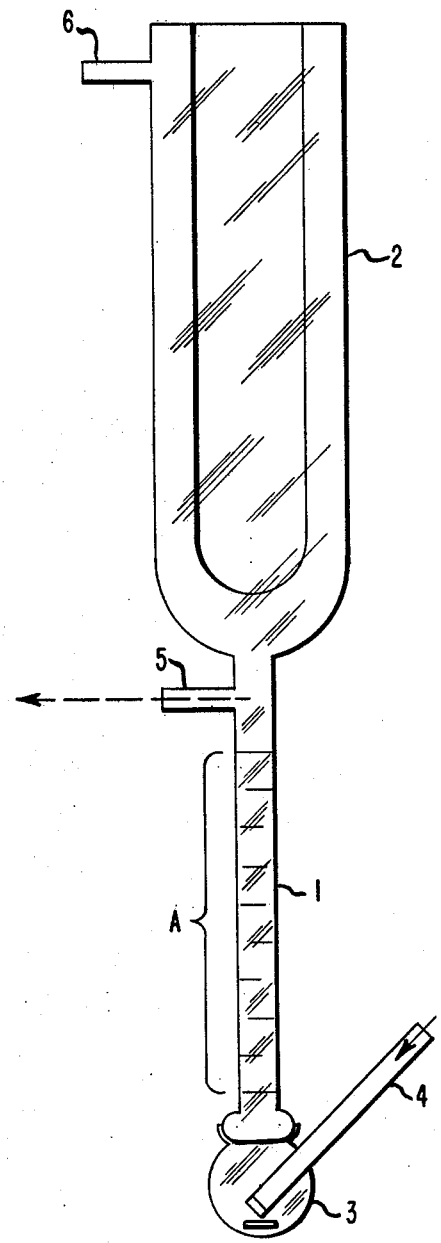
FIG. 1 is a drawing of a laboratory reactor suitable in operating the process of this invention.

A suitable laboratory apparatus for carrying out the process of the present invention is illustrated in FIG. 1. Reactor 1 is a glass tube packed with a sufficiently inert packing material, for example, HELI-PAK 3011 "HASTELLOY" B (Union Carbide Co.) stainless steel helices. The packed portion is indicated in this figure as A. A dry ice condenser, 2, is mounted on top of reactor 1, while a round-bottom flask, 3, is connected to the bottom of reactor 1. A gas inlet tube, 4, is sealed into the side of flask 3. This tube 4 serves as the HFPO inlet port and one of the nitrogen inlet ports. Side tube 6 is another nitrogen inlet port but sometimes may serve as a nitrogen exit port, and 5 is the HFA and a nitrogen exit port. Tube 5 is located above the packing zone A in reactor 1.

Figure 2:
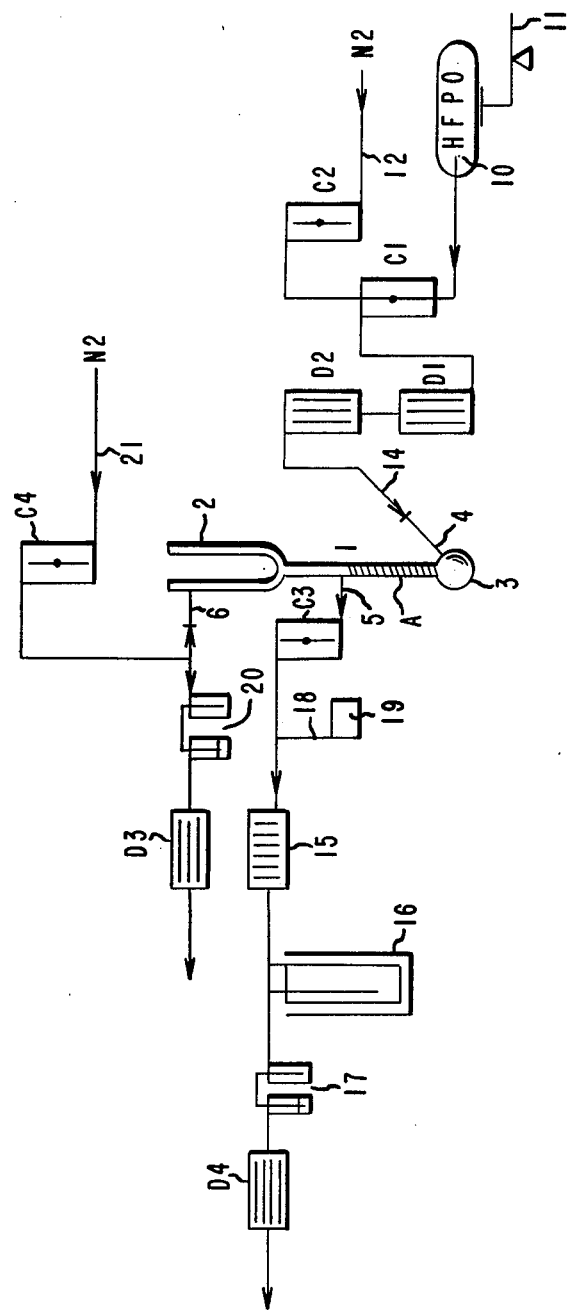
FIG. 2 is a flowsheet of one of the embodiments of the process of this invention.

A flowsheet of the complete process operation in laboratory equipment is shown in FIG. 2. Initially, the apparatus is purged with dry nitrogen entering via line 12 and port 4. Antimony pentafluoride is quickly introduced into flask 3, which is then cooled with dry ice-/acetone mixture, while nitrogen at a pressure of about 800–1733 Pa above atmospheric continues to be passed through lines 12 and 14 and port 4. The condenser 2 is charged with dry ice/acetone mixture; after a small amount of HFPO is fed into the flask 3 where it condenses, the bath around the flask is removed and the temperature rises. The flow of HFA, HFPO, and nitrogen entrains $SbF_5$ into reactor 1, where liquid $SbF_5$ is deposited on the packing in Zone A. Dry nitrogen is now introduced at a pressure of about 800–1733 Pa above atmospheric through line 21 and port 6, while the nitrogen flow through port 4 is reduced or stopped. At this time HFPO is delivered from cylinder 10 placed on scale 11 and enters through port 4. The rate of flow of HFPO is adjusted to give an appropriate reflux rate on top of reactor 1. HFA obtained by isomerization of HFPO in contact with $SbF_5$ in zone A of reactor 1 refluxes at about −27° C., but it may be at a lower temperature due to the cooling of liquefied HFA in contact with the dry ice/acetone cooled condenser 2 at about −80° C. The bottom portion of reactor 1 is maintained at a suitable temperature, for example, about 20°–130° C. At temperatures lower than 10° C., the isomerization rate is too low to be economical. Temperatures in excess of 150° C. often cause significant side product formation and thus are less desirable unless the contact time is very short. HFA formed in the reactor exits through port 5, passes through scrubber 15 and is collected in the dry ice trap 16; or, if the dry ice trap is omitted, it passes through the oil bubbler 17. Sample line 18 connects the HFA line with a gas sampling cell, 19, which can be transferred to an infrared spectrometer to determine product purity. Excess nitrogen escapes through mercury bubbler 20. In this figure C are rotameters, and D are drying columns (filled with anhydrous calcium sulfate, silica gel, or molecular sieves).

Under the conditions of this process, the isomerization of HFPO to HFA is very fast, so that the contact time will normally be below 5 minutes, especially below 1 minute, and particularly below 0.1 minute. The actual contact time will depend on a number of factors, including the desired rate of production of HFA, the amount of liquid antimony pentafluoride adsorbed on the solid support, the volume, and geometry of the catalyst support, and the temperatures and pressure within the reactor.

The HFPO feed rate should be high enough for obtaining a satisfactory HFA production rate. This can be as little as a weight of HFPO per hour equal to the weight of liquid $SbF_5$ in the catalyst but normally will be at least about twelve times and preferably at least twenty times as much. It is preferred to maintain HFPO feed rates at such a level that conversion of HFPO to HFA will be at least 99%. It is easy to determine experimentally the maximum desirable HFPO feed rate above which lower isomerization conversion is obtained. Naturally, the advantage of high conversion rates is high product purity, so that recycling or purification of the product is not necessary.

While the drawings and the examples illustrate an operation in glass equipment at essentially atmospheric pressure, an industrial operation would preferably be run at a pressure of about 689 kPa or greater. This would permit the use of water at about 25° C., rather than dry ice, for cooling. At this higher pressure HFA refluxing between the reactor packing and the water-cooled condenser provides adequate heat transfer to help control the reactor temperature and prevents loss of antimony pentafluoride. Vapor pressure curves can be used to determine the required pressure for a given cooling water temperature. For example, for cooling water at 35° C., the reactor pressure would be about 931 kPa. The reactor itself naturally can be operated at higher temperatures, within the broad range given earlier, but preferably not over 150° C. Since the isomerization reaction is exothermic, it usually will not be necessary to heat the reactor. Temperature control can be achieved, among others, by adjusting the following variables: the rate of reflux of HFA, the HFPO feed rate, the amount of external cooling of the reactor, and the temperature of the coolant in the condenser.

Many types of catalyst support materials can be used, but they must be reasonably inert under the process conditions and, especially, resistant to attack by liquid $SbF_5$. In addition to stainless steel, such as "HASTELLOY", suitable materials include, for example, various forms of elemental carbon, for example, activated carbon and graphite; ceramic materials and glass; and synthetic polymers, especially fluoropolymers such as polytetrafluoroethylene and copolymers of tetrafluoroethylene with hexafluroropropylene, perfluoro(propyl vinyl ether), and other comonomers. It is to be noted that graphite forms intercalation complexes with $SbF_5$. Those solid complexes are not suitable catalysts in the process of this invention. However, when an excess of $SbF_5$ is used, the uncomplexed liquid $SbF_5$ which remains adsorbed to or held by the solid support is an effective catalyst. It is advantageous to use a catalyst support that has a large surface area per unit of weight. On the one hand, such high surface materials adsorb liquid antimony pentafluoride very efficiently, and on the other hand, they improve the efficiency of contact between HFPO and the catalyst. Should any liquid $SbF_5$, nevertheless, be desorbed from its support by the gas stream flowing through the catalyst bed, it is retained within the reactor and returned to the catalyst bed with the refluxing hexafluoroacetone. It can be seen that the most favorable reactor configuration is vertical, as shown in FIGS. 1 and 2. This, naturally, is not a critical limitation, and the reactor can have any suitable shape and configuration, so long as substantially all of the antimony pentafluoride is retained within the reactor, rather than being gradually swept away by the gas flow.

Isomerization of HFPO to HFA is an exothermic reaction, but good contact is essential. A large scale, rapid batch reaction in a sealed ampoule according to the disclosure of the above-cited U.S. Pat. No. 3,213,134 would be difficult to control, especially in a system employing a high surface area, supported catalyst. The continuous process of the present invention, however, can be easily controlled and gives nearly quantitative yields of hexafluoroacetone.

This invention is now illustrated by representative examples of certain preferred embodiments thereof. All parts, proportions, and percentages are by weight, unless otherwise indicated.

A. The Equipment

A reactor was constructed of borosilicate glass substantially as shown in FIG. 1. The length of the column between the flask and the product take-off point (tube 5) was 14 cm, and the height of the packed section, A, was 10 cm. The inside diameter of the column was about 1 cm. Temperature was measured only at one point, on the outside wall of the column, at the bottom of the catalyst packing. Catalyst support was "HASTELLOY" B, "NICHROME" alloy, glass helices, activated charcoal, activated carbon, graphite or fluoropolymers including polytetrafluoroethylene. Valves, rotameters, and tubing connectors were made of 316 stainless steel. Rubber tubing was made of amber gum. Both "HASTELLOY" B and 316 stainless steel were to some extent corroded. The equipment, nevertheless, was operated regularly for six months without any major problems. Occasional equipment plugging was corrected by rinsing and blowing out.

B. Operation

The equipment was scrupulously dried under nitrogen from line 12 (FIG. 2) and then liquid antimony pentafluoride, 0.22 g (0.001 mole), was introduced into flask 3, which was connected to the reactor column. The product exit line 5 (FIG. 2) was closed at the rotameter C3, and flask 3 was chilled in a −80° C. dry ice/acetone mixture. The condenser 2 (FIG. 2) was then charged with a dry ice/acetone mixture, and HFPO was introduced into the flask. After condensing a small amount of HFPO in the flask, the dry ice bath was removed; the nitrogen flow from line 12 was reduced and nitrogen flow through tube 6 was started. HFA formed on warming and refluxed between the condenser and the packing. When the top portion of the packing was chilled to about −27° C. or less, the HFPO flow was adjusted to give 3–5 g per hour. Rotameter C3 was then adjusted so that the reflux was about 100 drops per minute, and HFA was removed from the reactor at about the same rate at which it was formed.

The base of catalyst packing A was maintained at 24°–33° C. The nitrogen bleed through tube 6 operated against mercury bubbler 20 providing a slight pressure to overcome the inertia of the downstream rotameter C3 and the slight back pressure of the oil bubbler 17. About 1-2 hours were required with this unit in order to attain a steady state; during this time the liqud SbF₅ was swept up and into the packing A.

Product gas samples were periodically collected for analysis. The purity of the product was determined by infrared analysis (especially in the regions of 5.3, 5.5, and 10 $\mu$m) and by gas chromatography. The purity of the product is dependent, among others, on the purity of the starting HFPO, which can vary from about 98% (the major impurity being hexafluoropropylene) to better than 99%.

The conditions and results obtained in seven different runs are shown in the following table:

TABLE

CONVERSION OF HFPO ON 10.3 g "HASTELLOY" B HELI-PAK 3011 PACKING

| Run No. | Liquid SbF₅ on the Packing (g)[a] | HFPO Flow Rate (g/hr) | HFPO (g/hr) SbF₅ (g) | Temp. at Base of Packing (°C.) | Reflux Rate (drops/min) | Conversion of HFPO to HFA (%) |
|---|---|---|---|---|---|---|
| 1 | 0.2 | 8.9 | 44.5 | 31 | 112 | 99.1 |
| 2 | 0.2 | 11.7 | 58.3 | 33 | 112 | 99.2 |
| 3 | 0.2 | 16.4 | 82 | 26 | 132 | 89.7 |
| 4 | 0.15 | 3.1 | 20.7 | 24 | 116 | 99.2 |
| 5 | 0.2 | 15.8 | 79 | 30 | 160 | 99.4 |
| 6 | 0.2 | 19.7 | 98.6 | 24 | 180 | 90.8 |
| 7 | 0.23[b] | 16.0 | 69.5 | 27 | 180 | 98.8 |

[a] These are the amounts weighed. In fact, a small amount of SbF₅ always was lost by volatilization before the steady state, so that the actual amounts were smaller than shown.
[b] In addition to the 10.3 g HASTELLOY B packing in the column A, there was 6.6 g of the packing in the flask 3.

It can be seen that, within the temperature range of 24°-33° C., conversion of HFPO to HFA was about 99% or better when the ratio of HFPO fed to SbF₅ catalyst was less than 82 (Runs 1, 2, 4, 5 and 7), In runs 3 and 6, where that ratio was 82 or more, the conversion was only about 90%. At other operating temperatures, the maximum practical HFPO (g/hr)/SbF₅ (g) ratio may be different, but it can be always readily ascertained.

I claim:

1. A process for the isomerization of hexafluoropropylene oxide to hexafluoroacetone comprising contacting in a reactor, at a temperature of about 10°-200° C., a stream of gaseous hexafluoropropylene oxide at an absolute pressure of about 0.103-13.79 MPa with a catalyst consisting essentially of liquid antimony pentafluoride adsorbed on a solid support; hexafluoroacetone being removed from the reactor at essentially the same rate as it is formed; and a portion of the reactor close to the hexafluoroacetone removal point being cooled to prevent loss of antimony pentafluoride.

2. The process of claim 1 wherein the weight of hexafluoropropylene oxide fed per hour is at least twelve times the weight of liquid SbF₅ adsorbed on a solid support.

3. The process of claim 2 wherein the weight of hexafluoropropylene oxide fed per hour is at least twenty times the weight of liquid SbF₅ adsorbed on a solid support.

4. The process of claim 1 wherein the feed rate of hexafluororpropylene oxide is such that conversion of hexafluoropropylene oxide to hexafluoroacetone is at least about 99%.

5. The process of claim 4 wherein the reactor in which the isomerization is carried out has a substantially vertical configuration.

6. The process of claim 5 wherein the lowest portion of the supported catalyst is at a temperature of at most about 150° C.

7. The process of claim 6 wherein the lowest portion of the supported catalyst is at a temperature of about 20°-130° C.

8. The process of claim 1 wherein the catalyst support has a large surface area per unit of weight.

9. The process of claim 1 which is conducted at a superatmospheric pressure with water cooling.

10. The process of claim 9 wherein the pressure is at least about 689 kPa.

* * * * *